United States Patent
Sprouse

(10) Patent No.: US 11,206,881 B2
(45) Date of Patent: Dec. 28, 2021

(54) FACE SHIELD SYSTEM

(71) Applicant: Brandon Sprouse, Seattle, WA (US)

(72) Inventor: Brandon Sprouse, Seattle, WA (US)

(*) Notice: Subject to any disclaimer, the term of this patent is extended or adjusted under 35 U.S.C. 154(b) by 0 days.

(21) Appl. No.: 17/210,976

(22) Filed: Mar. 24, 2021

(65) Prior Publication Data
US 2021/0321691 A1  Oct. 21, 2021

Related U.S. Application Data

(60) Provisional application No. 63/012,665, filed on Apr. 20, 2020.

(51) Int. Cl.
*A41D 13/11* (2006.01)

(52) U.S. Cl.
CPC ...... *A41D 13/1161* (2013.01); *A41D 13/1184* (2013.01)

(58) Field of Classification Search
CPC ............ A10D 13/1161; A10D 13/1184; A10D 13/1107; A61F 9/06; A41D 13/1161; A41D 13/1184; A41D 13/1107
USPC .............. 2/9, 10, 206, 195.1–195.4; 128/857
See application file for complete search history.

(56) References Cited

U.S. PATENT DOCUMENTS

| | | | | |
|---|---|---|---|---|
| 4,852,186 A * | 8/1989 | Landis | ............... | A41D 13/1184 2/9 |
| 4,867,178 A * | 9/1989 | Smith | ............... | A61F 9/02 128/858 |
| 4,884,296 A * | 12/1989 | Nix, Jr. | ............... | A61F 9/027 2/11 |
| 4,912,779 A * | 4/1990 | Laird | ............... | A61F 9/045 2/12 |
| 4,920,576 A * | 5/1990 | Landis | ............... | A41D 13/1184 2/9 |
| D899,002 S * | 10/2020 | Chapman | ............ | A41D 13/1184 D29/110 |
| 10,945,470 B1 * | 3/2021 | Maroofian | ......... | A41D 13/1107 |

(Continued)

OTHER PUBLICATIONS

Dezeen, "Simple origami face shield can be folded from single sheet of plastic," url: https://www.dezeen.com/2020/04/08/origami-face-shield-single . . . , dated Apr. 8, 2020.

*Primary Examiner* — Katherine M Moran
(74) *Attorney, Agent, or Firm* — Chambliss, Bahner & Stophel, P.C.; Stephen D. Adams

(57) ABSTRACT

A face shield system formed by a lay-flat headband removably joined with a lay-flat face shield. The headband having a first connection feature located at one end of the headband and a second connection feature located at an opposing end of the headband. The second connection feature removably connects with the first connection feature in order to provide a closed headband configured for placement around a user's head. A third connection feature is located between the first and second connection features. The face shield includes a fourth connection feature that removably engages with the third connection feature when the face shield is in a curved configuration in order to removably connect the headband together with the face shield. When the face shield is connected to the head band, a center of the face shield is spaced apart from a face of the user and a center of the headband.

12 Claims, 12 Drawing Sheets

(56) References Cited

U.S. PATENT DOCUMENTS

2005/0251890 A1\* 11/2005 Landis ................... A61F 9/045
2/9

\* cited by examiner

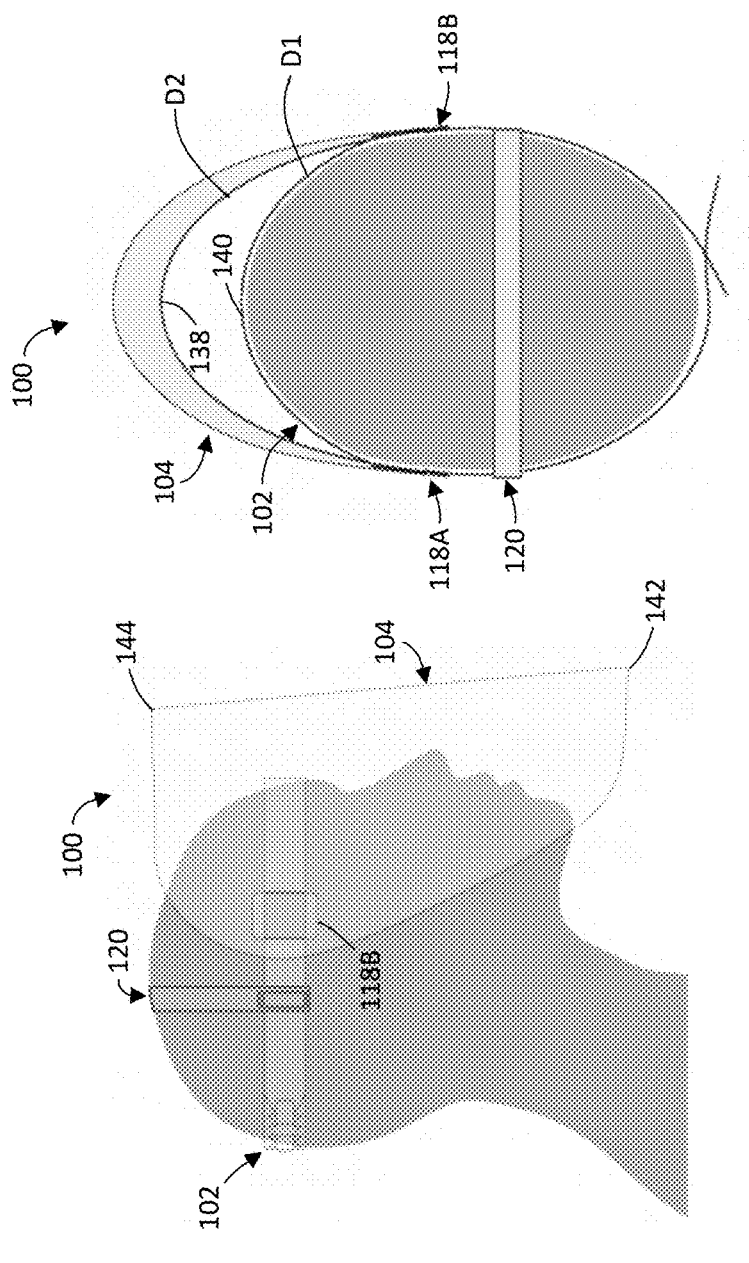
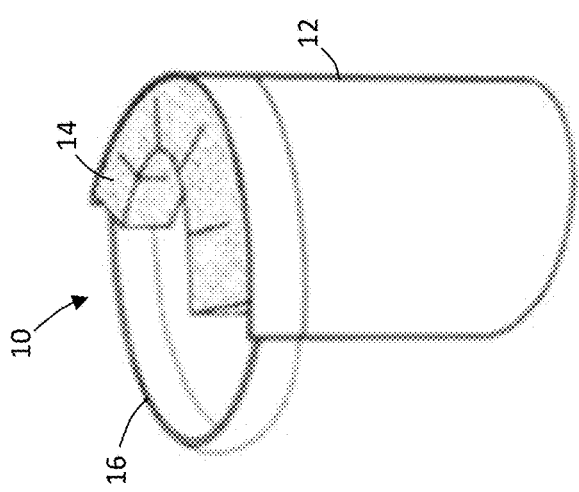
*FIGURE 3*
*FIGURE 2*
*FIGURE 1*
*(Prior Art)*

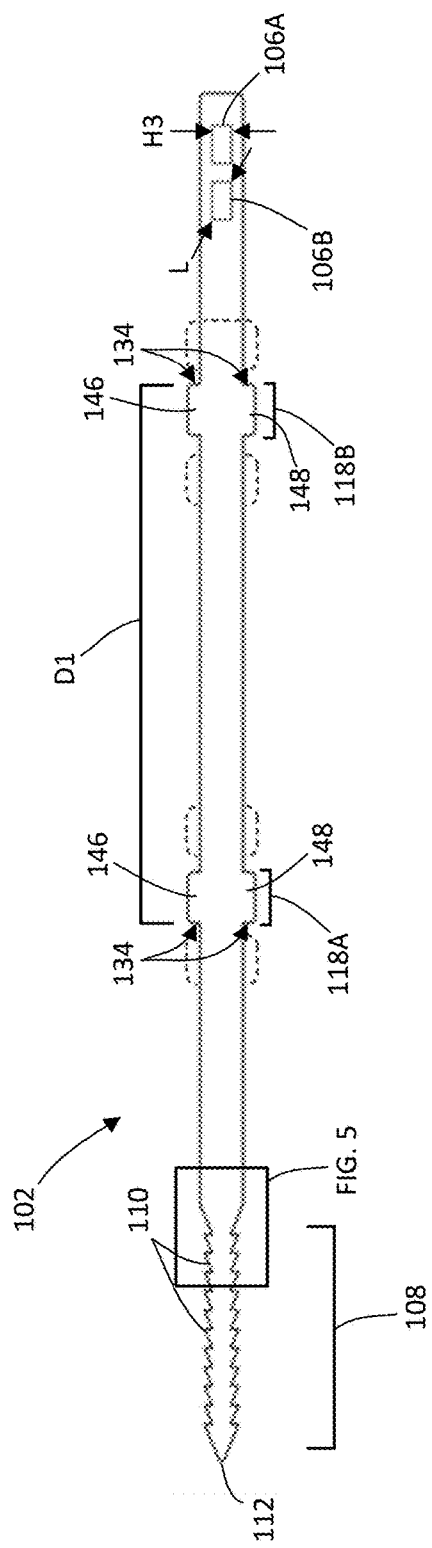
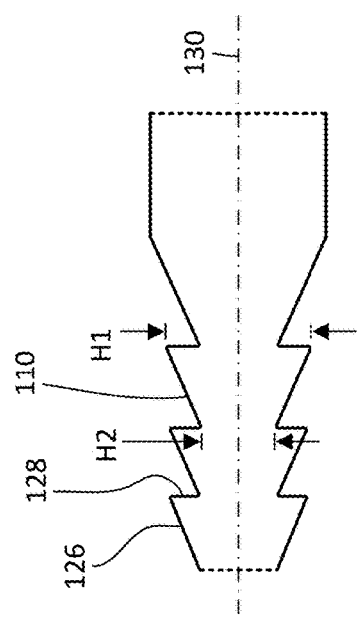
FIGURE 4
FIGURE 5

FACE SHIELD SYSTEM

CROSS-REFERENCE TO RELATED APPLICATIONS

This application claims the benefit of U.S. Provisional Application No. 63/012,665 filed Apr. 20, 2020, and entitled FACE SHIELD SYSTEM, which is incorporated herein by reference in its entirety.

FIELD

This invention relates generally to protective shielding systems designed to protect a user's face from foreign and/or dangerous contaminants while allowing the user to have the free use of his or her hands. More particularly, the present invention relates to a reusable two-piece face shield used to protect users against fluid-carried viruses and the like and that includes a headband and a removable face shield that may be collapsed and laid flat for easy transport and cleaning.

BACKGROUND

Helmets and masks used in the medical field are designed to limit the movement and transmission of contaminants in a work area in order to prevent or limit the spread of disease and limit infection. A recurring problem in the medical field is post-operative infections that result from the contamination of open wounds during surgery. In most cases, this type of infection can be prevented by providing medical workers with helmets and/or venting and filtering the surgical environment.

Another problem is that the diagnosis and care of patients with viral infections, such as coronavirus disease 2019 (i.e., COVID-19), at medical facilities, such as doctors' offices and hospitals, can result in the spread of that infection to medical workers and to other patients. These types of infectious diseases are often highly contagious and can be easily transmitted and spread when a person comes into contact with small droplets or aerosols, including those produced when another person coughs, sneezes and talks. These droplets may enter the eyes, nose, and oral cavity. These diseases may be spread through direct exposure, such as someone coughing or sneezing in the vicinity of another person, or through indirect exposure, such as by coming into contact with a surface where droplets are located. Certain viruses, such as the COVID-19 virus and flu viruses, can remain active or "live" on hard surfaces and remain transmissible for several hours or days. For this reason, a large percentage of those infected are infected by indirect contact with these viruses via surfaces (e.g., doors, windows, countertops, medical equipment, etc.), where droplets from an infected person were previously deposited.

Medical workers have attempted to limit their exposure to such infectious diseases through the use of personal protective equipment ("PPE"), such as gloves, masks, and protective face shields, such as the conventional face shield 10 shown in FIG. 1. This type of face shield is formed by a large plastic shield 12 that surrounds the user's face, including their eyes, nose, and mouth. The shield is held slightly in front of the user's face by a moisture (e.g., sweat) absorbent foam headband 14 that is placed inside of the shield and against the user's forehead. The combination of the shield and headband is secured in place on the user's head by an elastic band 16.

These types of face shields provide a full face covering that allows for unobstructed vision and free use of the user's hands and, for those reasons, they have worked very successfully for limiting exposure to bodily fluids and limiting the spread of infectious diseases in medical environments. However, they have a number of shortcomings that have become increasingly apparent with the worldwide spread of COVID-19, the drastic reduction in the availability of raw materials and manufacturing and transportation capabilities, and the large increase in the need for medical workers. A first issue, among others, is that there simply is not enough of this kind of face shield to meet the current demand. This shortage is aggravated by the fact that these conventional face shields 10 are often not "one size fits all" and the fact that the manufacturing process requires coordination of multiple supply chains in order to obtain the necessary raw materials.

Second, the construction of conventional face shields 10 is complicated and, for that reason, they typically come pre-assembled. To construct these conventional face shields 10, the various components must be connected together, which might require applying adhesive to connect the plastic shield 12 to the foam headband 14 and then installing a fastener to connect the headband to elastic band 16. Next, these face shields 10 are often provided with a range of small holes, slots corners, folds, etc. that enable the face shield to have a particular shape or contours and to provide certain functionality once assembled. However, these features add complexity and cost to the face shields 10 and, due to this complexity, the assembly process requires increased man hours and results in increased shipping and handling costs and space requirements. This translates into a high per unit cost for each of these face shields. The complexity of construction and need for pre-assembly also slows the production of new shields. Additionally, these face shields 10 are not easily assembled by a medical worker in the field that lacks the proper training or equipment to complete the assembly process.

Finally, these face shields are not easily disinfected. Due to supply shortage, many medical workers have attempted to re-use face shields during the current COVID-19 pandemic. However, this is complicated by the fact that the virus can be easily transmitted indirectly from surfaces. For that reason, many medical workers frequently attempt to disinfect and decontaminate their face shield and other PPE using chemical disinfectant wipes, etc. This is not an acceptable protocol under most normal circumstances, but it is necessary now for the reasons discussed above. This decontamination and reuse process is being performed on PPE that was not designed or intended to be decontaminated and reused and for that reason, the process is slow and is not always effective. For this reason, medical workers and others are still being infected from PPE that was believed to have been cleaned and disinfected. In the case of current face shield designs, the disinfecting process is complicated due to the holes, slots, corners, etc. discussed above that cannot easily be cleaned. Further, these conventional face shields 10 often use porous and absorbent materials (e.g., foam, elastic) in their construction that cannot be completely disinfected.

Accordingly, what is needed, is a face shield that can be quickly and easily manufactured and shipped, easily constructed and deconstructed by a person having minimal tools or training, and that can be easily and completely decontaminated.

Notes on Construction

The use of the terms "a", "an", "the" and similar terms in the context of describing embodiments of the invention are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic.

Terms concerning attachments, coupling and the like, such as "attached", "connected" and "interconnected", refer to a relationship wherein structures are secured or attached to one another either directly or indirectly through intervening structures, as well as both moveable and rigid attachments or relationships, unless otherwise specified herein or clearly indicated as having a different relationship by context. The term "operatively connected" is such an attachment, coupling or connection that allows the pertinent structures to operate as intended by virtue of that relationship.

The use of any and all examples or exemplary language (e.g., "such as" and "preferably") herein is intended merely to better illuminate the invention and the preferred embodiments thereof, and not to place a limitation on the scope of the invention. Nothing in the specification should be construed as indicating any element as essential to the practice of the invention unless so stated with specificity.

SUMMARY

The above and other problems are addressed by a face shield system that includes a lay-flat headband and a lay-flat face shield. The headband includes a first connection feature located at one end of the headband and a second connection feature located at an opposing end of the headband. The second connection feature is configured to removably connect with the first connection feature in order to provide a closed headband configured for placement around a user's head. A third connection feature is located between the first and second connection features. The face shield includes a fourth connection feature that is configured to removably engage with the third connection feature when the face shield is in a curved configuration in order to removably connect the headband together with the face shield and a center of the face shield is spaced apart from a face of the user and a center of the headband. In certain embodiments, the face shield system consists entirely and exclusively of the headband and the face shield.

In certain embodiments, the headband and face shield are each formed entirely from one identical type of flexible sheet material.

Certain embodiments include an elongate overhead strap having opposing ends. In those cases, each of the opposing ends is provided with a pair of slots and the headband and overhead strap are removably connected together by threading the headband through each pair of slots of the overhead strap.

In certain embodiments, the first connection feature includes a toothed section having a plurality of serrations with each serration having a maximum height H1 and a minimum height H2 and the second connection feature includes one or more openings formed in the headband and having a maximum height H3 that is at least equal to height H2 and less than height H1. In certain embodiments, the headband includes a plurality of first connection features that each sequentially engage and then disengage the second connection feature in order to adjust the size of the headband. In certain embodiments, the headband includes an initial second connection feature that is configured to be initially engaged by one of the plurality of first connection features and a subsequent second connection feature that is configured to be subsequently engaged by the one of the plurality of first connection features as the size of the headband is adjusted. In certain embodiments, the plurality of first connection features is engaged with the initial second connection feature to form a first connection point and, at the same time, a second one of the plurality of first connection features is engaged with the subsequent second connection feature to form a second connection point, such that the ends of the headband remain connected together even if one of the connection points is disconnected.

In certain embodiments, outermost edges are formed on each of the third connection features, which are spaced apart from one another by a distance D1. Additionally, outermost edges are formed on each of the fourth connection features, which are spaced apart from one another by a distance D2 that is greater than distance D1. The outermost edges of the fourth connection features contact the outermost edges of the third connection features when the third and fourth connection features are removably engaged.

In certain embodiments, the face shield substantially entirely covers the user's face when the face shield is removably engaged with the headband.

In certain embodiments, the third connection feature includes a separate tab section located at approximately a temple region of left and right sides of the user's head when the closed headband is placed onto the user's head. Each tab section includes an upper tab extending upward from a top of the headband and a corresponding lower tab that extends downwards from a bottom of the headband that is vertically aligned with the upper tab. The fourth connection feature includes tab receivers formed in the face shield that removably engage each of the tabs. In certain embodiments, the tab receivers each include one or more tab openings formed in the face shield into which the tabs may be removably inserted in order to removably connect the headband together with the face shield. In certain embodiments, each tab receiver includes an upper tab opening into which the upper tab is removably inserted and a lower tab opening into which the lower tab is inserted when the headband is removably connected together with the face shield. In certain embodiments, outermost edges are formed on each of the tabs and on each of the tab openings. The outermost edges of the tabs contact the outermost edges of the tab openings when the headband is removably connected together with the face shield.

In certain embodiments, the outermost edges of the tab openings are each canted inwards towards a center vertical axis of the face shield by an angle β measured from a vertical axis that is parallel to center vertical axis. When the headband is removably connected together with the face shield, a bottom end of the face shield is spaced laterally further from the headband than a top end of the face shield. In certain embodiments, angle β is greater than 0° and equal to or less than 20°.

In certain embodiments, the size of the headband may be adjusted by moving the one end of the headband with respect to the opposing end of the headband.

Certain embodiments further include a top shield for protecting a top portion of the user's head. The top shield is formed by a first folding panel that is joined continuously with a top edge of the face shield along a first joining line and a second folding panel that is joined continuously with a top edge of the first folding panel along a second joining line. The top shield is formed by folding the first folding panel downwards along the first joining line and folding the second folding panel upwards along the second joining line. In certain embodiments, the entire first joining line is straight and extends horizontally along the top edge of the face shield and the second joining line curves towards the first joining line. In certain embodiments, left and right sides of the first folding panel and the second folding panel and a top end of the second folding panel are each outwardly-bowed and bulbous. Additionally, a maximum unfolded width of the second folding panel is smaller than a maximum unfolded width of the first folding panel and the maximum unfolded width of the first folding panel is smaller than a maximum unfolded with of the face shield.

BRIEF DESCRIPTION OF THE DRAWINGS

Further advantages of the invention are apparent by reference to the detailed description when considered in conjunction with the figures, which are not to scale so as to more clearly show the details, wherein like reference numerals represent like elements throughout the several views, and wherein:

FIG. 1 is a front perspective view depicting a conventional face shield design;

FIG. 2 is a side elevation view depicting a user wearing a face shield system according to an embodiment of the present invention;

FIG. 3 is an overhead view depicting the user wearing the face shield system of FIG. 2;

FIG. 4 is a rear elevation view that depicts a headband used in constructing the face shield system of FIG. 2;

FIG. 5 depicts an enlarged portion of the headband of FIG. 4;

DETAILED DESCRIPTION

Figure 6:
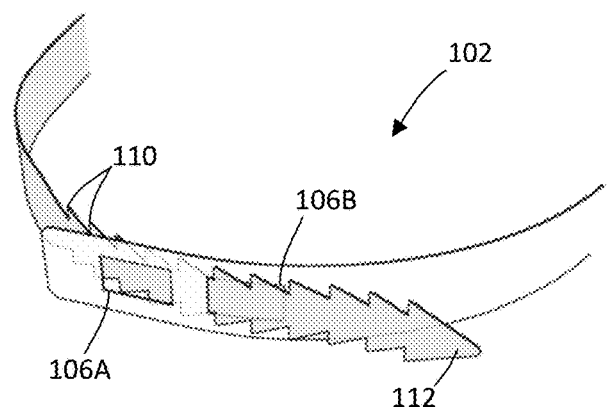
FIGS. 6-8 are top perspective views illustrating ends of the headband of FIG. 4 being connected together in three different embodiments of the present invention.

Referring now to the drawings in which like reference characters designate like or corresponding characters throughout the several views, there is shown in FIGS. 2 and 3 a face shield system 100 according to an embodiment of the present invention. In certain preferred embodiments, in order to simplify the manufacturing, shipping, and construction processes, the face shield system 100 is formed using only two components: a lay-flat headband 102 and a lay-flat face shield 104. In other embodiments, the system 100 also includes an optional lay-flat elongate overhead strap 120.

Each of these components is preferably formed utilizing the same type of material that is sourced from a single, continuous sheet material in order to simplify the manufacturing supply chain. In this case, the headband 102, face shield 104, and overhead strap 120 are formed using clear plastic sheeting that is thin enough to be manipulated (e.g., curved, folded, bent, etc.) but that is sufficiently thick and rigid to hold that manipulated shape without collapsing while in use. In preferred embodiments, the plastic sheeting used for the face shield system 100 is polyethylene terephthalate (PET) plastic and has a thickness of approximately 0.005 inch (i.e., 5 MIL) to approximately 0.025 inch (i.e., 25 MIL). In other embodiments, PET glycol-modified (PETG) or amorphous PET (APET) plastic, polycarbonates, or other similar materials suitable for use in medical equipment, or mixes thereof may be used in the construction of the face shield system 100.

In preferred embodiments, these materials are substantially non-porous and non-absorbent in order to limit absorption of contaminants into or admission of contaminants through the face shield system 100. Additionally, the headband 102, face shield 104, and strap 120 may be laid flat and both sides may be easily wiped clean and disinfected. Preferably, there are no small holes, slots, corners, etc. that cannot be easily cleaned. For example, each such hole, slot, corner, etc. is sized and configured to fit a finger or a disinfectant wipe. In this way, the face shield system 100 of the present invention is safer and simpler to keep clean than conventional face shields, such as the face shield 10 shown in FIG. 1. Additionally, it allows the face shield 104 to be easily packed, shipped, and then assembled with the headband 102.

As mentioned above, using only a single type of raw material simplifies the manufacturing supply chain, which reduces the overall costs and minimizes the time necessary to obtain the needed raw materials. Additionally, minimal manufacturing steps are needed to form these components. In preferred embodiments, the manufacturing process requires a single step of using a laser, die or other cutting process to cut the plastic sheeting into the two desired shapes. Lastly, as detailed below, the face shield system 100 may be easily assembled by the user using few steps, without any tools and with little or no instruction. For this reason, it is not necessary, or even desired, for the face shield to be sold and shipped in a pre-assembled state. Instead, all of the components of face shield system 100 may be flat packed (i.e., in a lay flat configuration) and shipped. This allows large quantities of face shields 100 to be quickly produced, shipped and stored using minimal space and incurring minimal cost.

Headband 102 is preferably formed as a flexible elongate strip having one or more first connection features located at one end and one or more second connection features located at the opposite end that are configured to removably but securely and preferably adjustable engage with the first connection features. In preferred embodiments, the size of the headband 102 may be adjusted by moving one end of the headband with respect to the opposing end of the headband. More particularly, in preferred embodiments, the headband 102 includes a plurality of first connection features that each sequentially engage and then disengage the second connection feature in order to adjust the size of the headband. In preferred embodiments, an initial second connection feature is initially engaged by one of the plurality of first connection features. Then, a subsequent second connection feature is subsequently engaged by the one of the plurality of first connection features as the size of the headband is adjusted. For example, a series of hooks or slots that engage with a corresponding series of hooks or slots may be formed at opposing ends of the headband 102. In certain embodiments, the first connection feature is engaged with the initial second connection feature to form a first connection point and, at the same time, a second one of the first connection features is engaged with the subsequent second connection feature to form a second and redundant connection point. Redundant connection points are provided such that the ends of the headband 102 remain connected together even if one of the connection points is disconnected. In the example given above, two hooks or slots on one end of the headband may be simultaneously joined together with two other hooks or slots located on the other end of the headband.

In the illustrated embodiment shown in FIGS. 4 and 5, one end of the headband 102 includes one or more sizing openings 106 (openings 106A and 106B are illustrated) and the opposite end of the headband is provided with a toothed section 108 that removably engages with the sizing openings. The toothed section 108 includes several serrations 110 that are preferably arranged in pairs along the length of the top and bottom edges of the toothed section. Each serration 110 is preferably formed by an inclined front edge 126 and a vertical rear edge 128. Preferably, a narrowed and pointed insertion tip 112 is located at the very end of the tooth section 108. Each pair of aligned serrations 110 of the toothed section 108 has a maximum height H1 and a minimum height 112. Preferably, maximum height H1 is measured from the outermost ends (when measured outwards from midline 130) of two aligned vertical rear edges 128 of two aligned serrations 110. Similarly, minimum height H2 is preferably measured from the innermost ends (when measured outwards from midline 130) of two aligned vertical rear edges 128 of two aligned serrations 110. Each of the sizing openings 106 has a maximum height 113 that is preferably approximately equal to or slightly larger than the minimum height H2 of the toothed section but less than the maximum height H1 of the toothed section.

Figure 7:
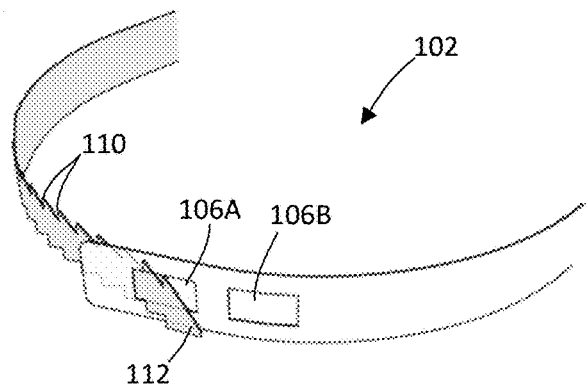
Figure 8:
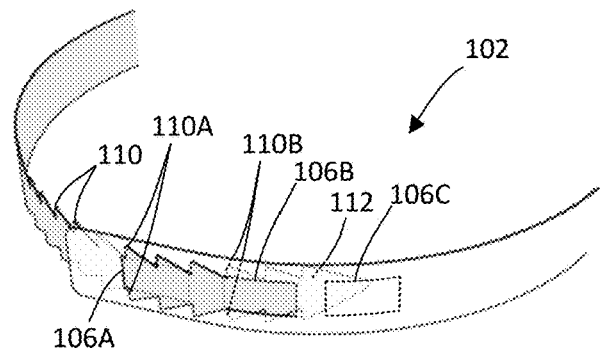

As shown in FIGS. 6-8, headband 102 is secured around a user's head by inserting and then pulling the insertion tip 112 through one of the sizing openings 106. The sizing opening 106 selected depends on the size of the user's head. For example, a user with a smaller head circumference might insert the insertion tip 112 through a "small" opening (e.g., opening 106B, as shown in FIG. 6), whereas a user with a larger head circumference might insert the insertion tip through a "large" opening (e.g., opening 106A, as shown in FIG. 7). Once the insertion tip 112 has been inserted through the selected opening 106, the insertion tip is grasped and then pulled until the headband 102 is sized to rest comfortably around the user's head. As the toothed section 108 is being pulled through a sizing opening 106, the inclined front edge 126 of each serration 110 passes through and may contact the opening. Once a pair of serrations 110 passes through an opening 106, corresponding vertical rear edges 128 of each serration come into contact with and rest against the opening. Since the maximum height H1 of the serrations 110 is larger than the maximum height H3 of the opening, the toothed section 108 is secured in the opening 106. Pulling the insertion tip 112 through opening 106A or opening 106B would result in an excess portion of the headband 102 extending away from the headband. Therefore, with reference to FIG. 8, in a preferred embodiment, this excess portion is inserted through an adjacent opening (e.g., opening 106B or another additional openings, such as opening 106C, provided along headband 102) such that the excess portion is located between the headband and the user's head.

In preferred embodiments, inserting the toothed section 108 back through an adjacent opening 106, as discussed above, not only serves as a means for securing the excess portion of the toothed section but also as a second (i.e., redundant) connection for the ends of the headband 102. As shown best in FIG. 8, the openings 106 and serrations 110 are sized and configured such that a first pair of aligned serrations 110A engages a first opening 106A on one side of the headband (i.e., outside of the headband) while, at the same time, a second pair of aligned serrations 110B engages a second opening 106B on the opposite side of the headband (i.e., inside of the headband) in the same manner. Thus, in preferred embodiments, a redundant connection is provided such that if one of the serration-opening connections fails, a second such connection will keep the face shield system 100 in place.

Referring again to FIGS. 2-5, when the headband 102 is properly sized and placed on the user's head, it will generally rest just above the brow and the top of the occipital bone of the user's skull. To take the headband 102 apart, the toothed section 108 may be curled (i.e., towards midline 130) in order to reduce its height such that the toothed section may be withdrawn from the opening 106. Additionally, the opening 106 may be provided with a length L (shown in FIG. 4) that is greater than the maximum height H1 of the toothed section 108. In the illustrated embodiment, length L is measured diagonally across the opening 106. As such, to remove the toothed section 108 from the opening 106, headband 102 may be rotated to align with length L and withdrawn. In other embodiments, length L may be measured horizontally (i.e., parallel with midline 130, shown in FIG. 5), which would result in an even longer diagonal measurement to further facilitate removal of the toothed section 108 from the opening 106. The openings 106 are shown in the illustrated embodiment as being rectangular in shape. However, in other embodiments, the openings 106 may be formed as rounded openings, as slots, or in other shapes or configurations.

Next, headband 102 is preferably also formed with a third connection feature located between the first and second connection features. More particularly, headband 102 is provided with two or more flexible tab sections 118 (FIG. 4) that are located between the sizing openings 106 and the tooth section 108. In the illustrated embodiment, a left tab section 118A and a right tab section 118B are illustrated. Other tab sections that are positioned at different locations along the headband 102 are shown in dashed lines. These other tab sections may be formed in addition to or in place of tab section 118A and 118B. Preferably, a tab section 118 is located at approximately a temple region of left and right sides of the user's head when the closed headband 102 is correctly placed onto the user's head. Preferably, each tab section 118 includes an upper tab 146 extending upward from a top of the headband 102 and a corresponding lower tab 148 that extends downwards from a bottom of the headband and is vertically aligned with the upper tab.

Figure 12:
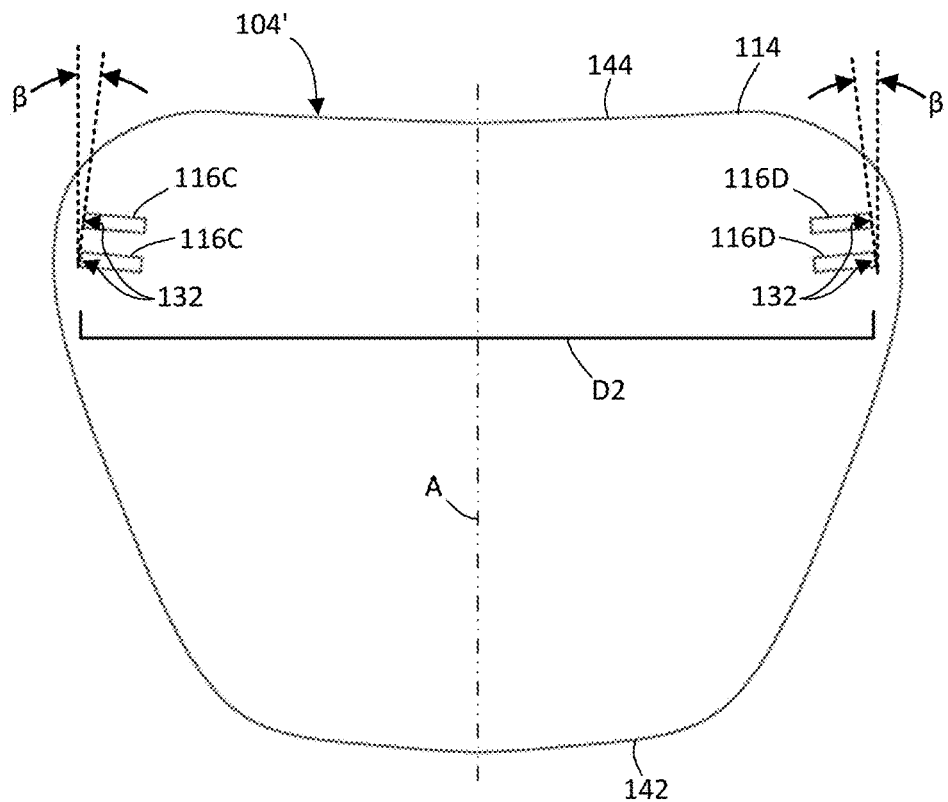
FIG. 12 is a rear elevation view that depicts an alternative face shield that may be used in constructing the face shield system of FIG. 2.
Figure 11:
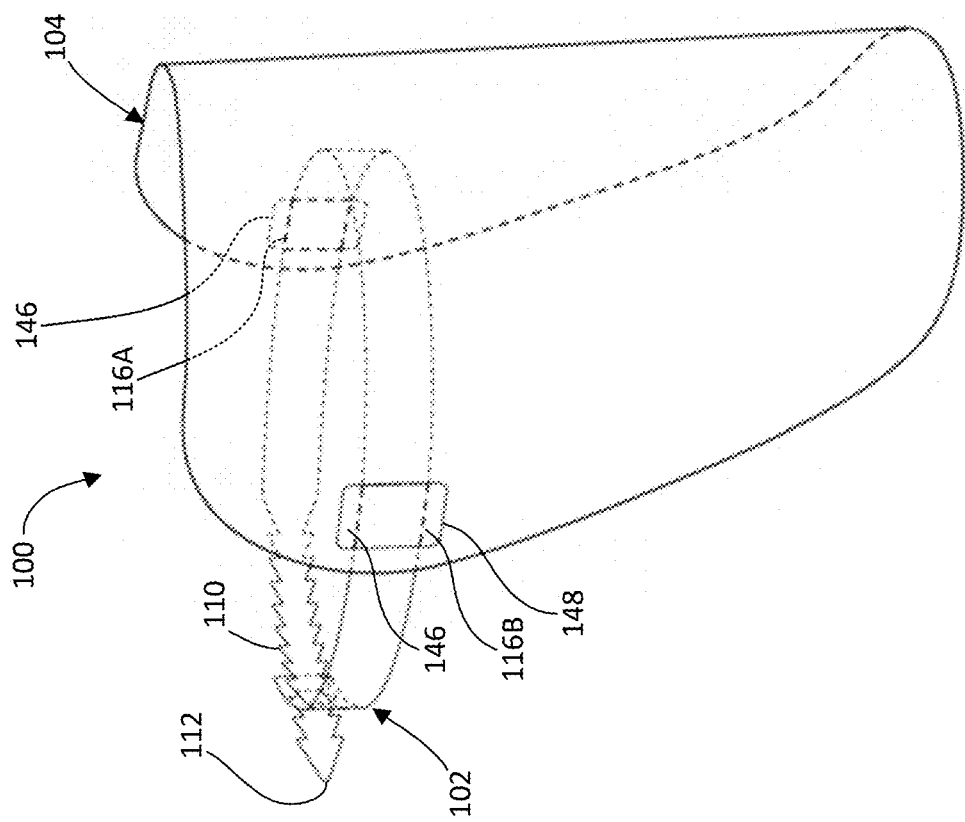
FIG. 11 is a front perspective view depicting the face shield system of FIG. 2 after insertion tabs have been inserted into corresponding tab openings.
Figure 13:
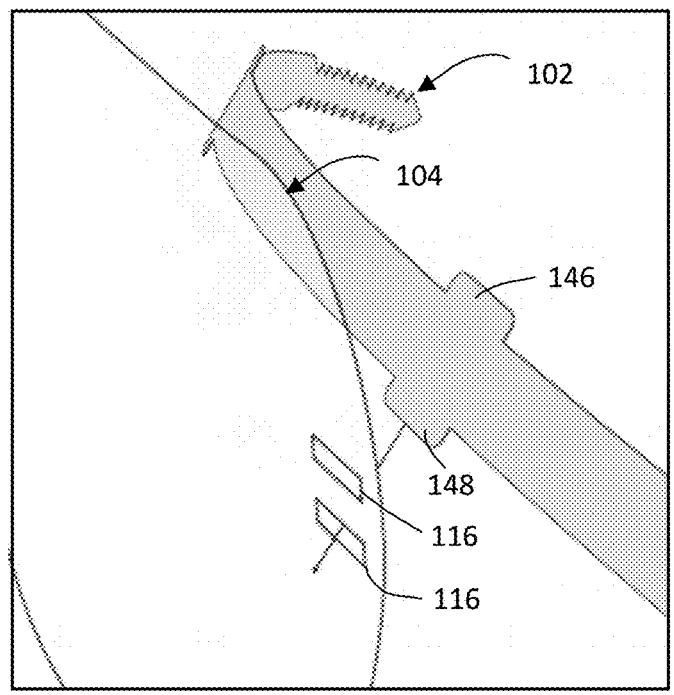
FIGS. 13 and 14 depict flexible tabs of a headband being inserted into tab openings in the face shield of FIG. 12.
Figure 14:
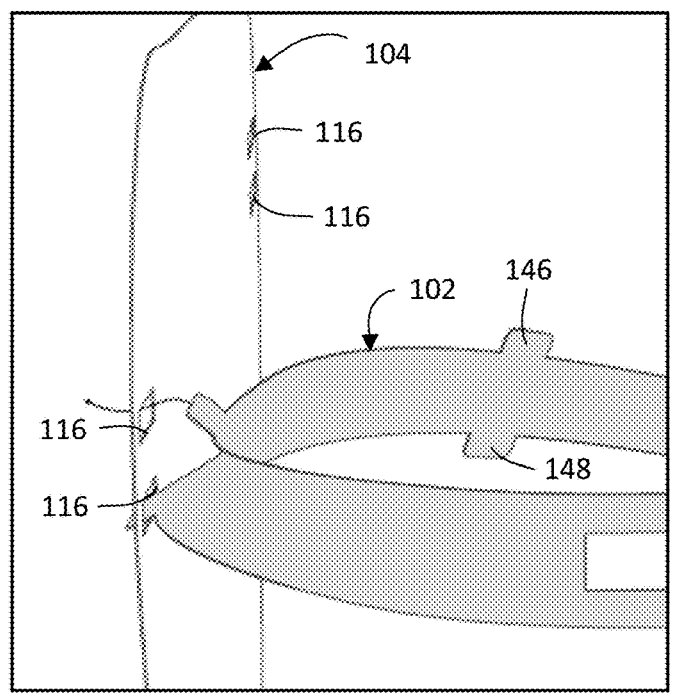

Face shield 104 is also preferably formed with a fourth connection feature that is configured to removably engage with the third connection feature in order to removably connect the face shield and headband 102 together. As an example, in the illustrated embodiment shown in FIGS. 9-11, tab openings 116 are located along the left and right edges of the face shield 104. More specifically, in this illustrated embodiment, a left tab opening 116A and a right tab opening 116B are shown. In use, tabs 146 and 148 are pressed into the tab openings 116 in order to removably connect headband 102 together with face shield 104. With reference to FIG. 12, face shield 104' is an alternative design that provides a pair of spaced apart left tab openings 116C and a pair of right tab openings 116D that are located along the left and right edges, respectively, of the face shield. These spaced apart tab openings 116C, 116D are smaller than openings 116A, 116B that were discussed previously and are intended to discourage users from incorrectly feeding the ends of the headband 102 itself through the openings (versus just the tabs 146, 148, as discussed above). Instead, as shown in FIGS. 13 and 14, tabs 146, 148 are configured to be pushed into and then retained by tab openings 116 in order to removably connect headband 102 together with face shield 104.

Figure 9:
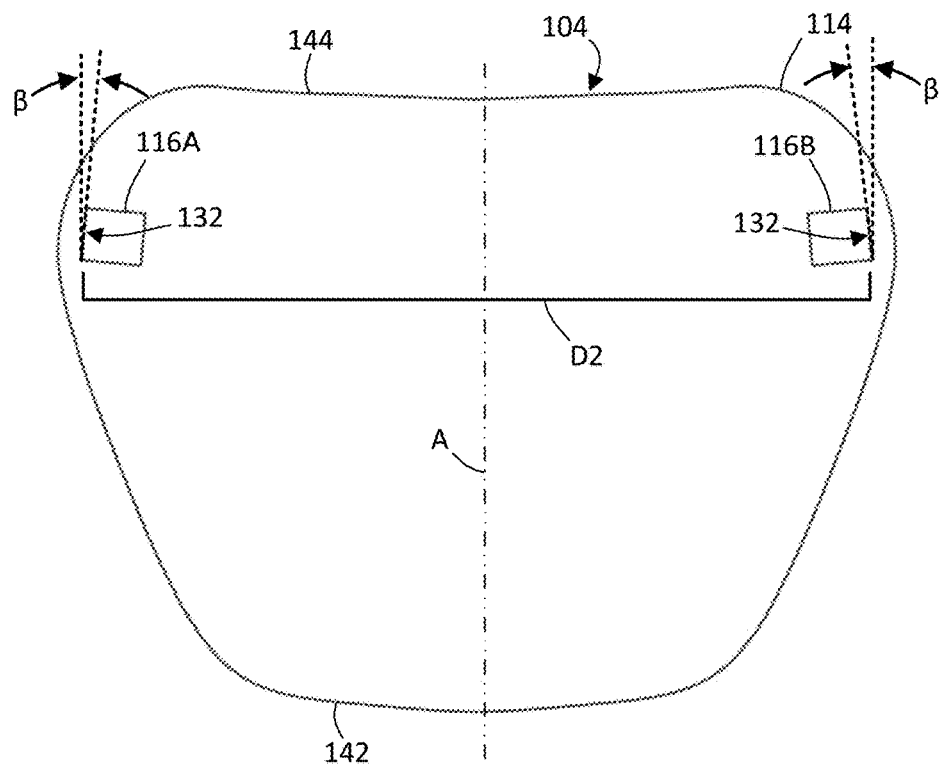
FIG. 9 is a rear elevation view that depicts a face shield used in constructing the face shield system of FIG. 2.
Figure 10:
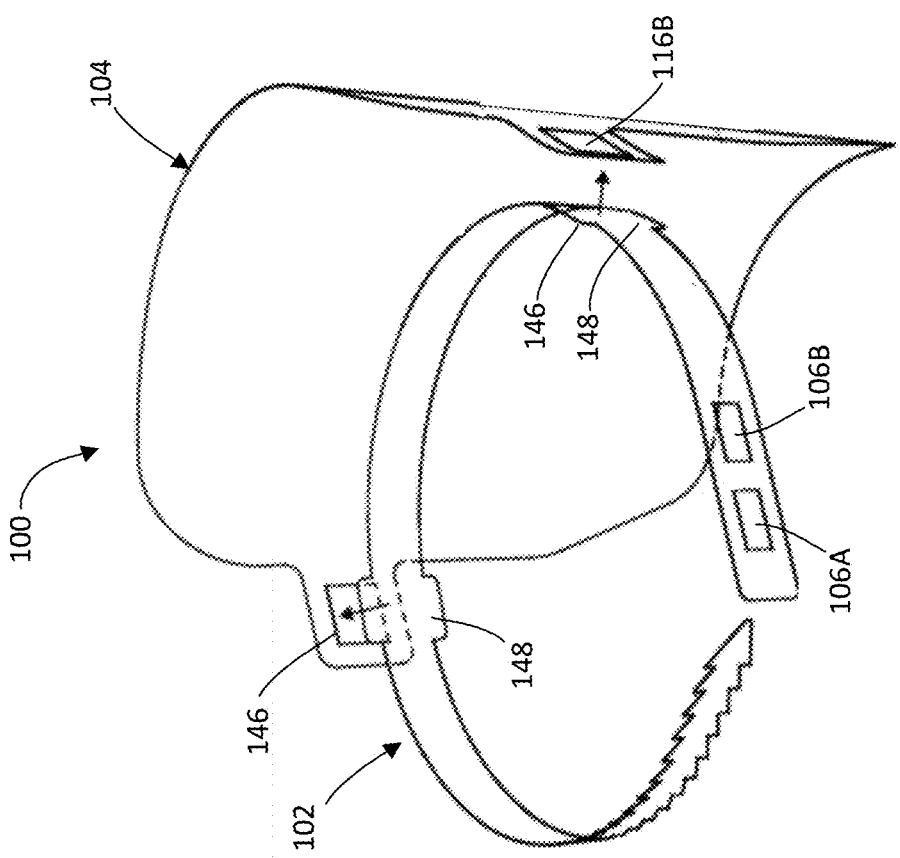
FIG. 10 is a rear perspective view that depicts insertion tabs of the headband of FIG. 4 being inserted into corresponding tab openings located in the face shield of FIG. 9 when forming the face shield system of FIG. 2.

In each of the above-described embodiments, (i.e., with face shield 104 or alternative face shield 104'), once tabs 146, 148 have been inserted into openings 116, the face shield 104 is held in place on the headband 102 when the outermost edge 132 (shown in FIGS. 9 and 12) of each of the tab openings 116 contacts the outermost edge 134 (shown in FIG. 4) of the tabs 146, 148. As a specific example, the left side 132 of tab opening 116A contacts the left side 134 of the tabs 146, 148 of left tab 118A section. Likewise, the right side 132 of right tab opening 116B contacts the right side 134 of the tabs 146, 148 of right tab section 118B. The outermost edges 134 of the tabs 146, 148 of left tab section 118A and the right tab 118B of headband 102 (measured from the outermost points) are separated by a horizontal distance D1 when laid flat. Similarly, as shown in FIGS. 9 and 12, the outermost edges 132 of tab openings 116 of face shield 104 (measured from the outermost points) are separated by a distance D2 when laid flat. More generally, distances D1 and D2 represent the lateral distance across the headband 102 and face shield 104, respectively, separating the points at which the headband connects to the face shield.

The face shield 104 is preferably held in a curved configuration when removably connected with the headband 102. Additionally the center 138 of face shield 104 is spaced away from the center 140 of headband 102 whenever distance D1 is less than distance D2. As distance D1 converges with distance D2 (or as distance D2 converges with distance D1), the face shield 104 is drawn closer in towards the headband 102 (and the user). Conversely, as distance D1 diverges from distance D2 (or as distance D2 diverges from distance D1), the face shield 104 is pushed further outwards from the headband 102 (and the user). It is preferred, but not required, that when the face shield system 100 is in use, the left tab section 118A is positioned approximately at or just in front of the user's left temple and the right tab section 118B is positioned approximately at or just in front of the user's right temple. As such, it is preferred that distance D1 be approximately equal to the distance separating the user's left and right temples, when measured along the sides of the head and across the forehead. Additionally, it is preferred that the face shield 104 be spaced away from the user's face. As such, it is preferred that distance D2 is greater than distance D1. In certain preferred embodiments, distance D2 is 5%-10% greater than distance D1. In other preferred embodiments, distance D2 is 10%-25% greater than distance D1. In other preferred embodiments, distance D2 is more than 25% greater than distance D1.

Additionally, as shown in FIGS. 9 and 12, in certain preferred embodiments including the illustrated embodiment, to further assist in spacing the face shield 104 away from the user's face, each of the tab openings 116 may be angled or canted inwards. In this particular embodiment, openings 116 are canted inwards towards the center of the face shield 104 such that the outermost edge 132 is oriented at an angle β of greater than 0° to equal to or less than 20° with respect to vertical axis that is parallel to center vertical axis A. This slight angle causes the face shield 104 to be sloped (as shown in FIG. 2), where the bottom end 142 of the face shield is spaced laterally further from the headband 102 than the top end 144 of the face shield.

Face shield 104 has a contoured perimeter or edge 114, whose shape is symmetrical about center vertical axis A. When the face shield 104 is in use, axis A is aligned with the center of a user's face and the face shield curves outwards from axis A. In preferred embodiments, when the face shield system 100 is in use, the face shield 104 preferably follows the general shape of the user's face. More preferably, the face shield 104 "substantially entirely" covers the user's face by extending from below the chin, upwards to the cheekbone, around the temple, and then upwards above the top of the head. The face shield 104 preferably extends from behind the user's temples to a position that is spaced away from the front of the user's face, including the user's eyes, nose and mouth, in order to protect the user against the spray and transmission of fluids.

Figure 15:
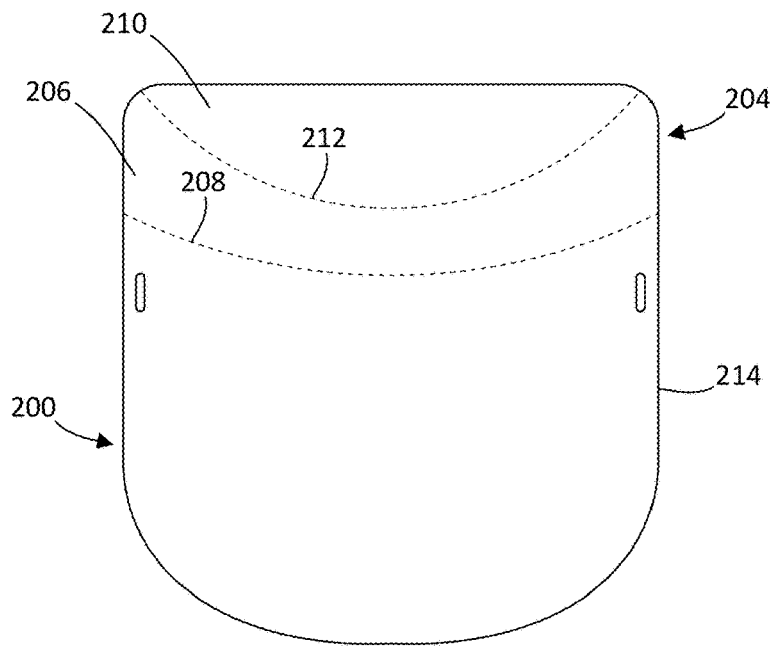
FIG. 15 is a front elevation view depicting a conventional face shield having a top shield formed by folding upper panels that are formed by a pair of curved score lines, shown in an unfolded configuration.
Figure 16:
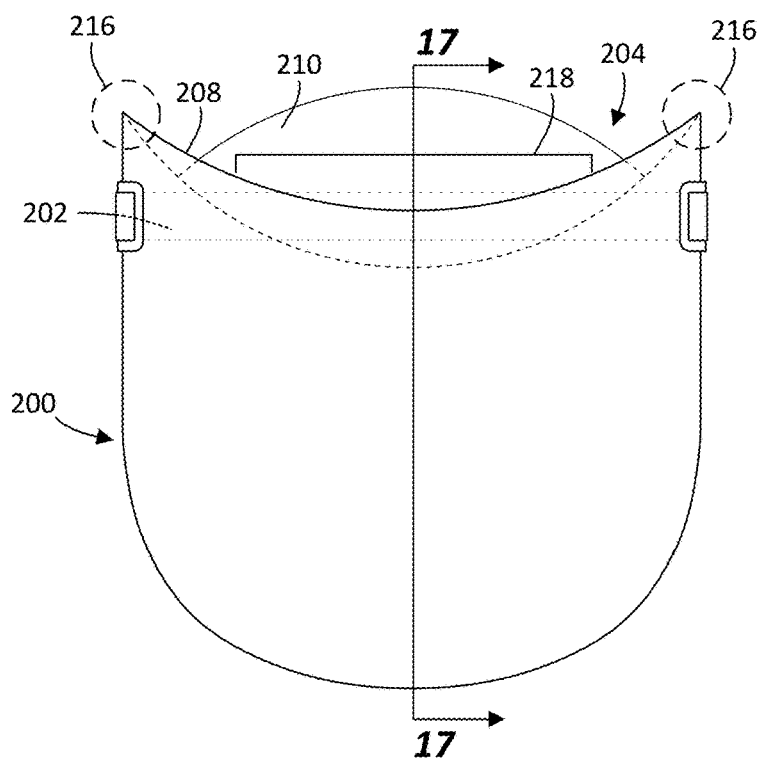
FIG. 16 is a front elevation view depicting the conventional face shield of FIG. 15 in a folded configuration and including a headband.
Figure 21:
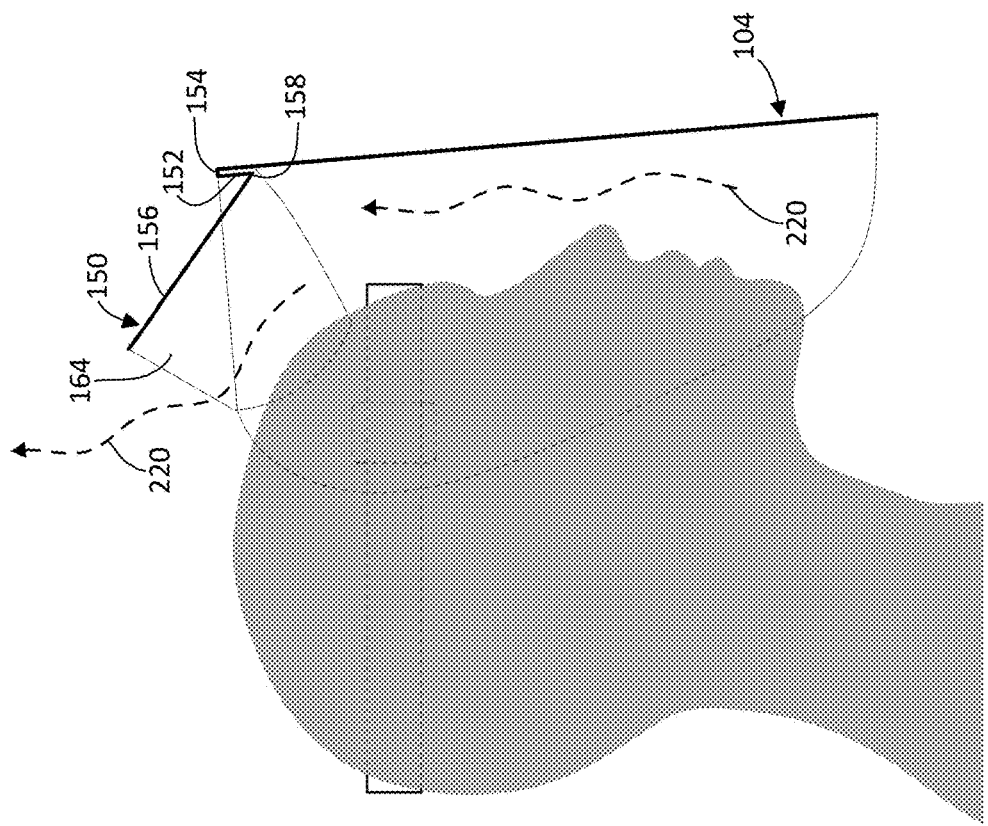
FIG. 21 is a sectional view of the face shield of FIG. 20 taken along line 21-21 and also showing a user in profile wearing the face shield.
Figure 17:
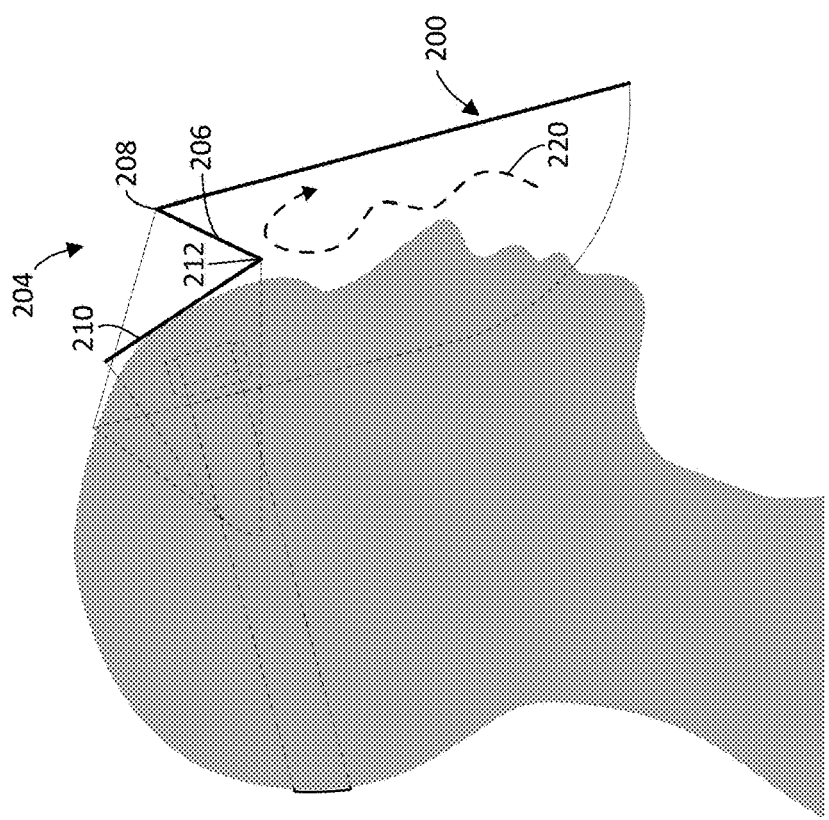
FIG. 17 is a sectional view of the face shield of FIG. 15 taken along line 17-17 and also showing a user in profile wearing the face shield.
Figure 18:
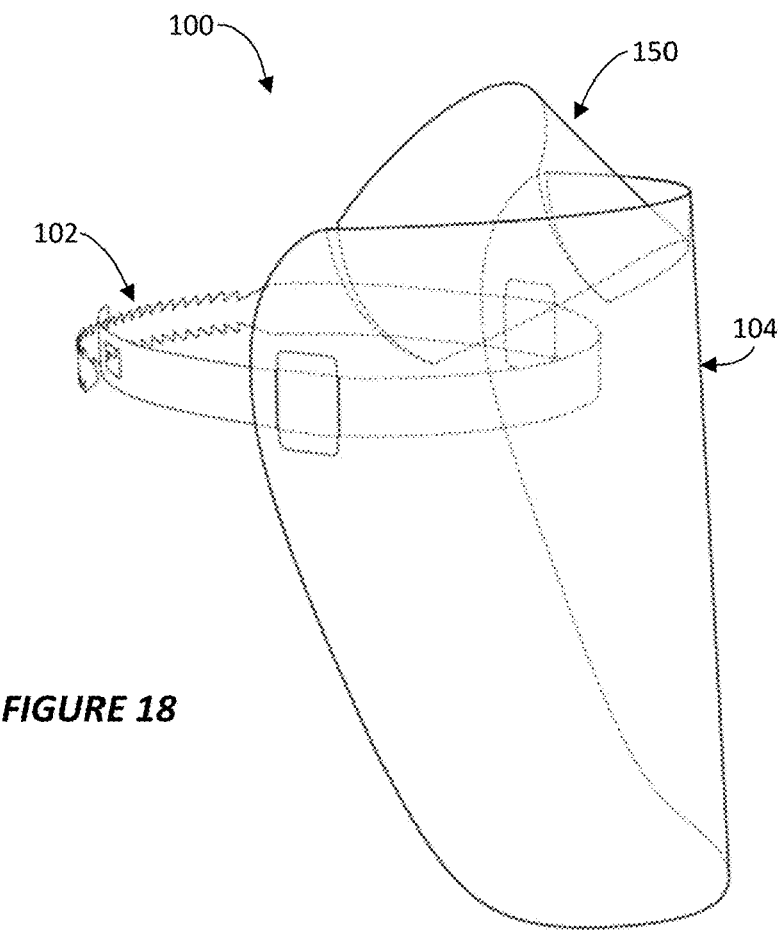
FIG. 18 is a perspective view depicting a face shield system having a face shield with folding upper panels for providing a top shield that are formed by a straight score line and a curved score line and a headband according to alternative embodiment of the present invention, shown in an folded configuration.

For additional protection again the spray and transmission of fluids, certain face shield systems are provided with a top shield. For example, with reference to FIGS. 15-17, a conventional face shield 200 and conventional elastic headband 202 are illustrated. Face shield 200 includes a top shield 204 that is formed by a first panel 206 that is joined to the top of the face shield at a curved first scoring line 208 and a second panel 210 that is joined to the top of the first panel at a curved second scoring line 212. Face shield 200 defined by a continuous or straight perimeter edge 214. Each of the scoring lines 208, 212 curve downwards towards the face shield 200, which permits the panels 206, 210 to be folded. However, there are a number of issues associated with this convention design. First, the elastic headband 202 is not a fixed length and, instead, continuously places a compressive force onto the head of the user, which becomes increasingly uncomfortable to the user. Next, due to the curvature of the first scoring line 208, pointed or "horned" shaped ends 216 are formed at the left and right ends of the face shield 200 and a downwardly-curved portion 218 connects the horned ends, where both of the scoring lines 208, 212 curve downwards towards the user's head. This curved shape is opposite the curvature of the contour of the human head, which results in an odd fitment of the face shield with the human head. Additionally, as shown best in FIG. 17, the curved first scoring line 208 also limits how closely the first panel 206 can be folded behind the face shield 200. As shown the first panel 206 is angled away from and is not substantially parallel with the face shield 200. This, in turn, forces the second panel 210 rearwards (i.e., towards the user's face) away from the face shield 200 such that it is pressed against the top of the user's head. When the second panel 210 contacts the user's head or face, heat and moisture 220 becomes trapped under the face shield 200 and first panel 206, which causes the face shield 200 to fog over. In some cases, an anti-fog agent is applied to the surface of the face shield 200. However, this anti-fog agent is often washed away or becomes cloudy when the face shield 200 is cleaned and sanitized.

Now, with reference to FIGS. 18-25, there is shown face shields 104 having top shields 150 according to embodiments of the present invention. In preferred embodiments, top shield 150 is formed from a first folding panel 152 that is joined continuously with a top edge of the face shield 104 along a first joining line 154 and a second folding panel 156 that is joined continuously with a top edge of the first folding panel along a second joining line 158. Top shield 150 is preferably formed by folding the first folding panel 152 downwards along the first joining line 154 and then folding the second folding panel 156 upwards along the second joining line 158. In preferred embodiments, the entire first joining line 154 is straight and extends horizontally along the top edge of the face shield 104 and the second joining line 158 curves towards the first joining line. In certain embodiments, the joining lines 154, 158 are continuous scores or creases formed into the top shield 150 material. In other cases, discontinuous or perforated scored sections (vs. continuous scored sections) form the joining lines 154, 158. An advantage of providing a horizontal first joining line 154 is that, when curved, the face shield 104 and top shield 150 more accurately conform to the shape of the user's head. In particular, an upwardly-curved portion 160 is located at the center of the face shield 104, where the second folding panel 156 curves upwards away from and around the top of the user's head in an unfolded configuration.

Additionally, in preferred embodiments, left and right sides 160 of the first folding panel and the second folding panel and a top end 162 of the second folding panel are each outwardly-bowed and bulbous. In an alternative embodiment, alternative left and right sides 160' are straight and extends upwards to the top end 162. In preferred embodiments, a maximum unfolded width of the second folding panel 156 is smaller (i.e., narrower) than a maximum unfolded width of the first folding panel 152. Additionally, a maximum unfolded width of the first folding panel 152 is smaller (i.e., narrower) than a maximum unfolded with of the face shield 104. The provides a more aesthetically pleasing appearance when the face shield with top shield 150 are in use that more accurately follows the shape of the user's face. More importantly, the tapering sides 160 enable a "tighter" fit and allows for the sides of the face shield 104 and top shield 150 to curl more closely around the user's face in order further limit exposure to airborne particles, etc. Additionally, the horizontal joining line 154 enables the first folding panel 152 to be folded at the first joining line 154 and brought much closer to the face shield 104 compared to the prior art. In preferred embodiments, the first folding panel 152 is substantially parallel with the face shield 104 when folded at joining line 154. This in turn, allows for the second folding panel 156 to be located further away from the user's face such that a gap 164 is provided between the top shield and the user through which heat and moisture 220 may escape from under the face shield 104 and top shield 150. This, of course, helps to prevent the face shield 104 from fogging.

Figure 26:
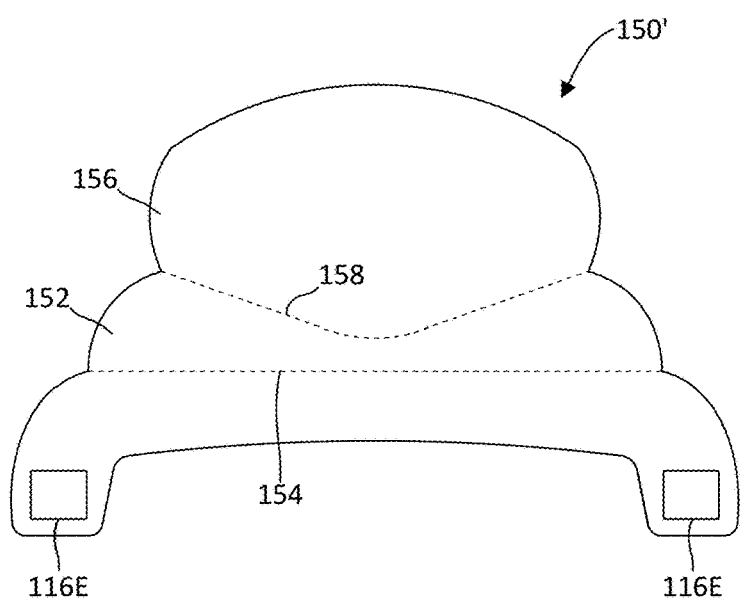
FIG. 26 is a front elevation view depicting a removable top shield for use in connection with a face shield according to an embodiment of the present invention.
Figure 19:
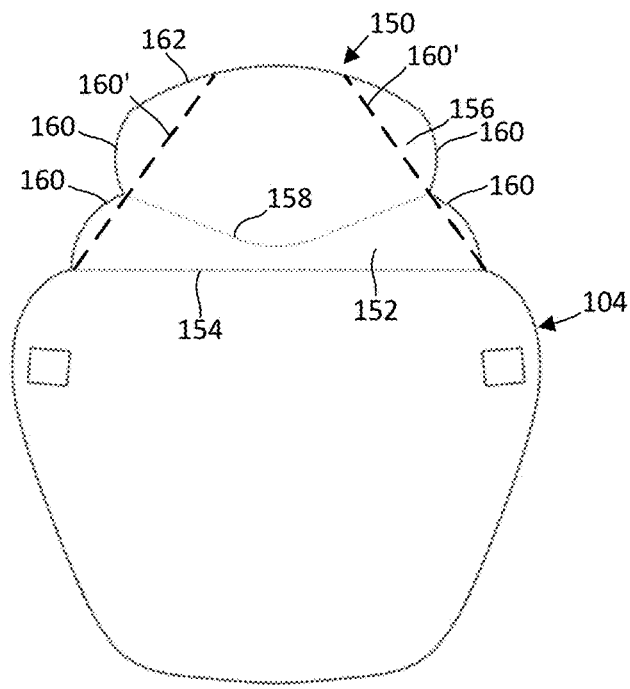
FIG. 19 is a front elevation view depicting the face shield of FIG. 18, shown in a unfolded configuration.
Figure 20:
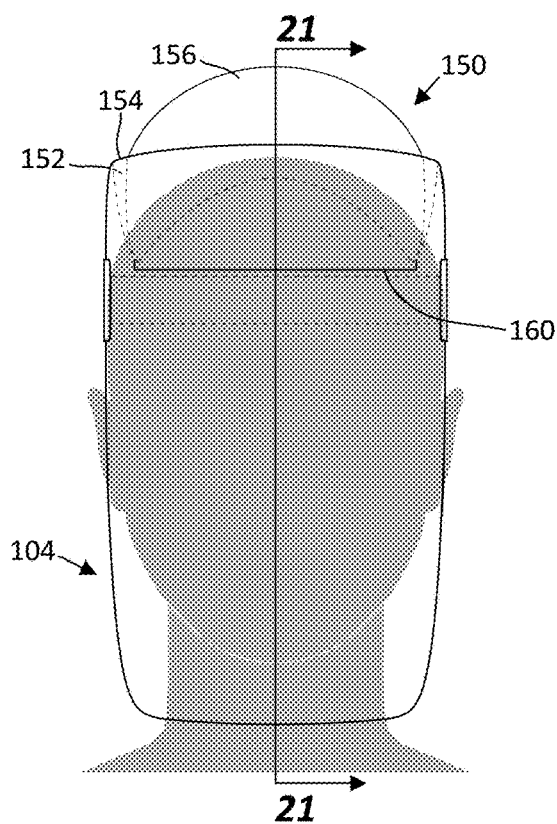
FIG. 20 is a front elevation view depicting the face shield of FIG. 18, shown in a folded configuration.
Figure 25:
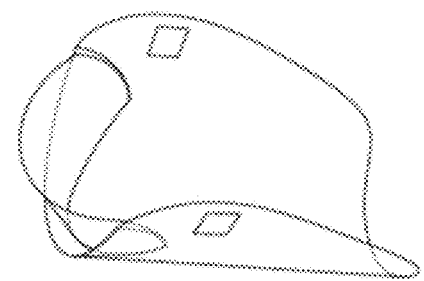
FIGS. 22-25 are rear perspective views depicting the face shield of FIG. 18 being converted from the unfolded configuration to a folded configuration.
Figure 24:
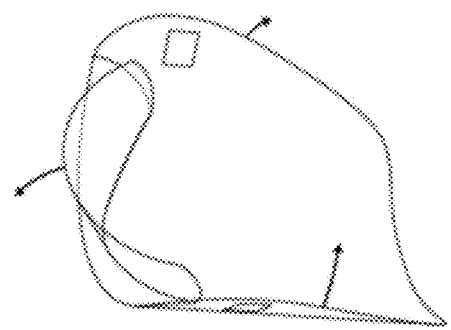
Figure 23:
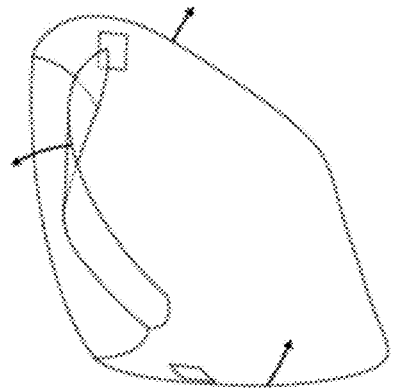
Figure 22:
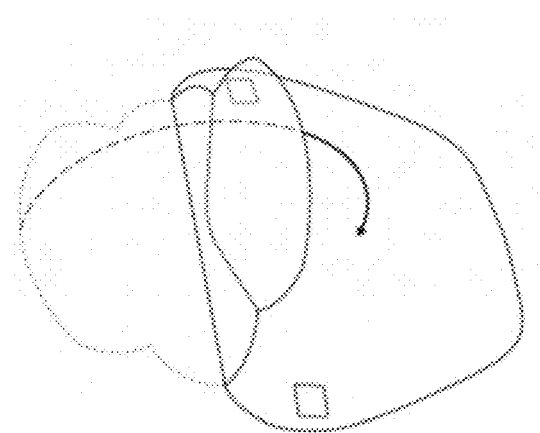

With reference to FIG. 26, there is provided a removable top shield 150' according to an embodiment of the invention. Top shield 150' is almost structurally and functionally identical to top shield 150. The primary difference is that top shield 150' includes a headband section 166 that is joined to the first folding panel 152 along first horizontal joining line 154 in place of face shield 104. Headband section 166 includes a fifth connection feature that is configured to removably engage with the third connection feature of the headband and the fourth connection feature of the face shield in order removably connect the headband section, headband, and face shield together. In this particular embodiment, tab openings 116E provided on left and right ends of the headband section 166 are located such that the tabs 146, 148 of the headband 102 may be inserted into the tab openings 116E and also inserted into openings 116A-116D.

Figure 27:
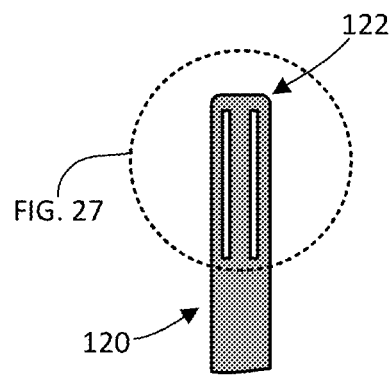
FIGS. 27 and 28 depict an end of an optional overhead strap that may be placed onto the headband of FIGS. 2 and 3.
Figure 28:
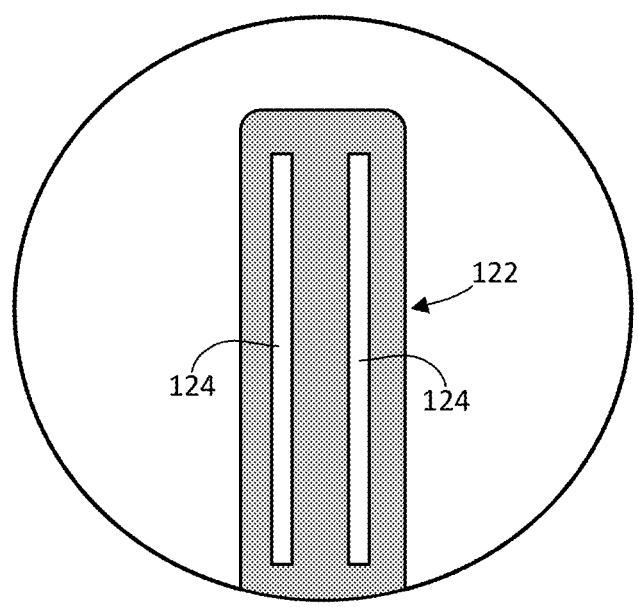

The first step to using the presently-disclosed face shield system 100 is to attach the head band 102 to the face shield 104. As discussed above, this is accomplished by pushing the tabs 118 through tab openings 116. Since distance D1 is less than distance D2, connecting the head band 102 to the face shield 104, the front portion of the face shield is curved outwards such that it separated from the head band. Next, the face shield 104 is secured over the user's face. This is accomplished by inserting the insertion tip 112 of the head band 102 through the appropriate sizing opening 106 and then pulling the end of the head band through the sizing opening by the insertion tip. As the insertion tip 112 is pulled, the serrations 110 will automatically engage the sizing opening 106 to create an opening for the user's head having a smaller and smaller circumference to securely hold the face shield in front of the user's face. These steps are reversed to disassemble the face shield system 100. Advantageously, once the face shield system 100 is disassembled, the headband 102 and the face shield 104 are disconnected from each other and may be laid flat (i.e., "lay-flat") and both sides may be easily wiped clean and disinfected. Finally, referring again to FIGS. 2 and 3 and with further reference to FIGS. 27 and 28, there is shown optional overhead strap 120 that may be placed onto a headband 102 for keeping the face shield system 100 in place on a user's head. Opposing ends 122 of the strap 120 are preferably provided with a pair of slots 124 that allows opposite ends of the headband 102 to be threaded through the strap.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations as would be appreciated by those having ordinary skill in the art to which the invention relates.

What is claimed is:

1. A face shield system comprising:
    a lay-flat headband configured to be laid flat, the headband having:
        a first connection feature located at one end of the headband;
        a second connection feature located at an opposing end of the headband, wherein the second connection feature is configured to removably connect with the first connection feature in order to provide a closed headband configured for placement around a user's head;
        a pair of third connection features provided between the first and second connection features;
    a lay-flat face shield configured to be laid flat, the face shield having a top end and a bottom end and a fourth connection feature located proximate each of the left and right ends of the face shield that are each configured to removably engage with one of the third connection features when the face shield is in a curved configuration in order to removably connect the headband together with the face shield;
    a front portion of the face shield extending between the fourth connection features and extending from the top end to the bottom end of the face shield, wherein when the fourth connection features are engaged with the third connection features, the front portion of the face shield is separated from and does not contact the headband in order to provide a gap between the front portion of the face shield and the headband; and
    an elongate overhead strap having opposing ends, wherein each of the opposing ends is provided with a pair of slots and wherein the headband and overhead strap are removably connected together by threading the headband through each pair of slots of the overhead strap.

2. A face shield system comprising:
    a lay-flat headband configured to be laid flat, the headband having:
        a first connection feature located at one end of the headband and comprising a toothed section having a plurality of serrations with each serration having a maximum height H1 and a minimum height H2;
        a second connection feature located at an opposing end of the headband and comprising one or more openings formed in the headband and having a maximum height H3 that is at least equal to height H2 and less than height H1, wherein the second connection feature is configured to removably connect with the first connection feature in order to provide a closed headband configured for placement around a user's head;
        a pair of third connection features provided between the first and second connection features;
    a lay-flat face shield configured to be laid flat, the face shield having a top end and a bottom end and a fourth connection feature located proximate each of the left and right ends of the face shield that are each configured to removably engage with one of the third connection features when the face shield is in a curved configuration in order to removably connect the headband together with the face shield; and
    a front portion of the face shield extending between the fourth connection features and extending from the top end to the bottom end of the face shield, wherein when the fourth connection features are engaged with the third connection features, the front portion of the face shield is separated from and does not contact the headband in order to provide a gap between the front portion of the face shield and the headband.

3. The face shield system of claim 2 further comprising an insertion tip formed at one of said ends of the headband and located adjacent the plurality of serrations, wherein, after the insertion tip is pulled through one of the one or more openings in the headband, each of the plurality of serrations is configured to sequentially engage and then disengage the one opening in order to adjust the size of the headband.

4. A face shield system comprising:
    a lay-flat headband configured to be laid flat, the headband having:
        a first connection feature located at one end of the headband;
        a second connection feature located at an opposing end of the headband, wherein the second connection feature is configured to removably connect with the first connection feature in order to provide a closed headband configured for placement around a user's head;
        a pair of third connection features provided between the first and second connection features;
    a lay-flat face shield configured to be laid flat, the face shield having a top end and a bottom end and a fourth connection feature located proximate each of the left and right ends of the face shield that are each configured to removably engage with one of the third connection features when the face shield is in a curved configuration in order to removably connect the headband together with the face shield;
    a front portion of the face shield extending between the fourth connection features and extending from the top end to the bottom end of the face shield, wherein when the fourth connection features are engaged with the third connection features, the front portion of the face shield is separated from and does not contact the headband in order to provide a gap between the front portion of the face shield and the headband;
    outermost edges formed on each of the third connection features that are spaced apart from one another by a distance D1; and
    outermost edges formed on each of the fourth connection features that are spaced apart from one another by a distance D2 that is greater than distance D1 wherein the outermost edges of the fourth connection features contact the outermost edges of the third connection features when the third and fourth connection features are removably engaged.

5. A face shield system comprising:
    a lay-flat headband configured to be laid flat, the headband having:
        a first connection feature located at one end of the headband;
        a second connection feature located at an opposing end of the headband, wherein the second connection feature is configured to removably connect with the first connection feature in order to provide a closed headband configured for placement around a user's head;
        a pair of third connection features provided between the first and second connection features;
    a lay-flat face shield configured to be laid flat, the face shield having a top end and a bottom end and a fourth connection feature located proximate each of the left and right ends of the face shield that are each configured to removably engage with one of the third connection features when the face shield is in a curved configuration in order to removably connect the headband together with the face shield;

a front portion of the face shield extending between the fourth connection features and extending from the top end to the bottom end of the face shield, wherein when the fourth connection features are engaged with the third connection features, the front portion of the face shield is separated from and does not contact the headband in order to provide a gap between the front portion of the face shield and the headband;

wherein the third connection feature comprises a separate tab section located at approximately a temple region of left and right sides of the user's head when the closed headband is placed onto the user's head, wherein each tab section includes an upper tab extending upward from a top of the headband and a corresponding lower tab that extends downwards from a bottom of the headband and is vertically aligned with the upper tab; and wherein the fourth connection feature comprises tab receivers formed in the face shield adapted to removably engage each of the tabs.

6. The face shield system of claim 5 wherein the tab receivers each comprise one or more tab openings formed in the face shield into which the tabs may be removably inserted in order to removably connect the headband together with the face shield.

7. The face shield system of claim 6, wherein each tab receiver comprises an upper tab opening into which the upper tab is removably inserted and a lower tab opening into which the lower tab is inserted when the headband is removably connected together with the face shield.

8. The face shield system of claim 6 further comprising:
outermost edges formed on each of the tabs;
outermost edges formed on each of the tab openings, wherein the outermost edges of the tabs contact the outermost edges of the tab openings when the headband is removably connected together with the face shield.

9. The face shield system of claim 8 wherein the outermost edges of the tab openings are each canted inwards towards a center vertical axis of the face shield by an angle β measured from a vertical axis that is parallel to center vertical axis, such that, when the headband is removably connected together with the face shield, a bottom end of the face shield is spaced laterally further from the headband than a top end of the face shield.

10. The face shield system of claim 9 wherein angle β is greater than 0° and equal to or less than 20°.

11. A face shield system comprising:
a lay-flat headband configured to be laid flat, the headband having:
a first connection feature located at one end of the headband;
a second connection feature located at an opposing end of the headband, wherein the second connection feature is configured to removably connect with the first connection feature in order to provide a closed headband configured for placement around a user's head;
a pair of third connection features provided between the first and second connection features;
a lay-flat face shield configured to be laid flat, the face shield having a top end and a bottom end and a fourth connection feature located proximate each of the left and right ends of the face shield that are each configured to removably engage with one of the third connection features when the face shield is in a curved configuration in order to removably connect the headband together with the face shield;
a front portion of the face shield extending between the fourth connection features and extending from the top end to the bottom end of the face shield, wherein when the fourth connection features are engaged with the third connection features, the front portion of the face shield is separated from and does not contact the headband in order to provide a gap between the front portion of the face shield and the headband; and
a top shield for protecting a top portion of the user's head, the top shield formed by a first folding panel that is joined continuously with a top edge of the face shield along a first joining line and a second folding panel that is joined continuously with a top edge of the first folding panel along a second joining line,
wherein the top shield is formed by folding the first folding panel downwards along the first joining line and folding the second folding panel upwards along the second joining line, and
wherein the entire first joining line is straight and extends horizontally along the top edge of the face shield and the second joining line curves towards the first joining line.

12. The face shield system of claim 11 wherein left and right sides of the first folding panel and the second folding panel and a top end of the second folding panel are each outwardly-bowed and bulbous, wherein a maximum unfolded width of the second folding panel is smaller than a maximum unfolded width of the first folding panel, and wherein the maximum unfolded width of the first folding panel is smaller than a maximum unfolded with of the face shield.

* * * * *